(12) United States Patent
Kreikebaum et al.

(10) Patent No.: US 7,752,930 B2
(45) Date of Patent: Jul. 13, 2010

(54) MICROBIAL GASEOUS-FLUID SAMPLER AND METHOD OF OPERATING THE SAME

(75) Inventors: Gerhard Kreikebaum, San Bernardino, CA (US); David L. Chandler, Highland, CA (US); Justin F. Dean, San Bernardino, CA (US)

(73) Assignee: Venturedyne, Ltd., Pewaukee, WI (US)

( * ) Notice: Subject to any disclaimer, the term of this patent is extended or adjusted under 35 U.S.C. 154(b) by 199 days.

(21) Appl. No.: 11/549,259

(22) Filed: Oct. 13, 2006

(65) Prior Publication Data

US 2008/0087108 A1    Apr. 17, 2008

(51) Int. Cl.
*G01N 1/22* (2006.01)
(52) U.S. Cl. .................................... 73/863.23
(58) Field of Classification Search ............. 73/863.21, 73/863.71–73, 864, 864.51, 863.03
See application file for complete search history.

(56) References Cited

U.S. PATENT DOCUMENTS

| | | | | |
|---|---|---|---|---|
| 3,295,359 | A | * | 1/1967 | Peck .......................... 73/28.04 |
| 4,067,705 | A | * | 1/1978 | Kurz ........................ 73/863.03 |
| 4,389,903 | A | | 6/1983 | Bertone et al. |
| 4,961,916 | A | * | 10/1990 | Lesage et al. ................. 422/88 |
| 5,001,463 | A | | 3/1991 | Hamburger |
| 5,245,318 | A | | 9/1993 | Tohge et al. |
| 5,410,403 | A | | 4/1995 | Wells |
| 5,456,102 | A | | 10/1995 | Moorehead |
| 5,861,053 | A | | 1/1999 | Noritake et al. |
| 6,119,531 | A | | 9/2000 | Wendte et al. |
| 6,167,766 | B1 | | 1/2001 | Dunn et al. |
| 6,514,721 | B2 | | 2/2003 | Spurrell |
| 6,564,655 | B1 | | 5/2003 | Austen et al. |
| 6,604,405 | B2 | | 8/2003 | Whynall et al. |
| 6,656,430 | B2 | | 12/2003 | Sheppard, Jr. et al. |
| 6,741,056 | B1 | | 5/2004 | Hall |
| 6,867,413 | B2 | * | 3/2005 | Basch et al. ................. 250/255 |
| 6,887,710 | B2 | | 5/2005 | Call et al. |
| 6,938,502 | B2 | | 9/2005 | Tanoshima et al. |
| 6,947,134 | B2 | | 9/2005 | Chang et al. |
| 2002/0124664 | A1 | | 9/2002 | Call et al. |
| 2003/0070498 | A1 | | 4/2003 | Ohyama et al. |
| 2004/0103727 | A1 | | 6/2004 | Erlach et al. |
| 2004/0125371 | A1 | | 7/2004 | Chang et al. |
| 2005/0074361 | A1 | | 4/2005 | Tanoshima et al. |
| 2005/0074904 | A1 | | 4/2005 | Chin et al. |
| 2006/0000296 | A1 | | 1/2006 | Salter |

* cited by examiner

*Primary Examiner*—Hezron Williams
*Assistant Examiner*—Mark Shabman
(74) *Attorney, Agent, or Firm*—Michael Best & Friedrich LLP

(57) ABSTRACT

A portable microbial gaseous-fluid sampler includes a gaseous-fluid flow system at least partially supported by a structure. The gaseous-fluid flow system includes a gaseous-fluid intake portion having an intake port, a blower in fluid communication with the intake port, and a gaseous-fluid exhaust portion having an exhaust port. The sampler can further include an exhaust filter operable to substantially filter a totality of the gaseous fluid flowing through the sampler prior to exhausting the gaseous fluid. The sampler also can include a control system operable to control at least gaseous-fluid flow through the sampler, and a remote sampling head.

18 Claims, 6 Drawing Sheets

MICROBIAL GASEOUS-FLUID SAMPLER AND METHOD OF OPERATING THE SAME

BACKGROUND

The invention relates to microbial gaseous-fluid sampler and methods of operating the same. Commonly, such microbial gaseous-fluid samplers can be microbial air samplers operable to capture bacteria, fungi, and other particles onto a Petri dish loaded with nutrient agar. The sample captured onto the Petri dish can be grown into colonies. The colonies formed after incubation are counted to determine the concentration of colony forming units (CFU's).

SUMMARY

In one embodiment, the invention provides a microbial gaseous-fluid sampler for collecting microbial particles from gaseous fluid. The sampler includes a base unit having a structure and a gaseous-fluid flow system at least partially supported by the structure. The sampler also includes a remote sampling head at a remote location from the base unit and in fluid communication with an intake port of the base unit. The remote sampling head is configurable to collect at least a portion of the microbial particles from a sample of the gaseous fluid at the remote location.

In another embodiment, the invention provides a portable microbial gaseous-fluid sampler for collecting microbial particles from gaseous fluid. The sampler includes a structure and a gaseous-fluid flow system at least partially supported by the structure. The gaseous-fluid flow system includes a gaseous-fluid exhaust portion having an exhaust port and an exhaust filter operable to substantially filter a totality of the gaseous fluid flowing through the sampler prior to exhausting the gaseous fluid.

In another embodiment, the invention provides a portable gaseous-fluid sampler for collecting microbial particles from gaseous fluid. The sampler includes a structure and a gaseous-fluid flow system at least partially supported within the structure. The gaseous-fluid flow system includes a gaseous-fluid intake portion having an intake port, a blower in fluid communication with the intake port, and a gaseous-fluid exhaust portion having an exhaust port. The sampler also includes a control system operable to at least in part control the blower to selectively adjust the gaseous-fluid flow through the sampler. The control system includes a mass-flow sensor to sense a characteristic relating to gaseous-fluid flow through the sampler.

In another embodiment, the invention provides a method of controlling gaseous-fluid flow through a portable microbial gaseous-fluid sampler. The sampler includes a gaseous-fluid flow system. The method includes generating gaseous-fluid flow through the gaseous-fluid flow system, and collecting at least a portion of the gaseous-fluid flow. The method also includes generating a signal based on the collecting at least a portion of the gaseous-fluid flow, and comparing the signal to a reference signal.

In another embodiment, the invention provides a portable gaseous-fluid sampler for collecting microbial particles from gaseous fluid. The sampler includes a structure and a gaseous-fluid flow system at least partially supported by the structure. The gaseous-fluid flow system includes a gaseous-fluid intake portion having an intake port, a blower in fluid communication with the intake port, and a gaseous-fluid exhaust portion having an exhaust port. The sampler further includes a control system operable to at least in part control the blower to selectively adjust the gaseous-fluid flow through the sampler. The control system includes a differential pressure transducer to sense a characteristic relating to gaseous-fluid flow through the sampler.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
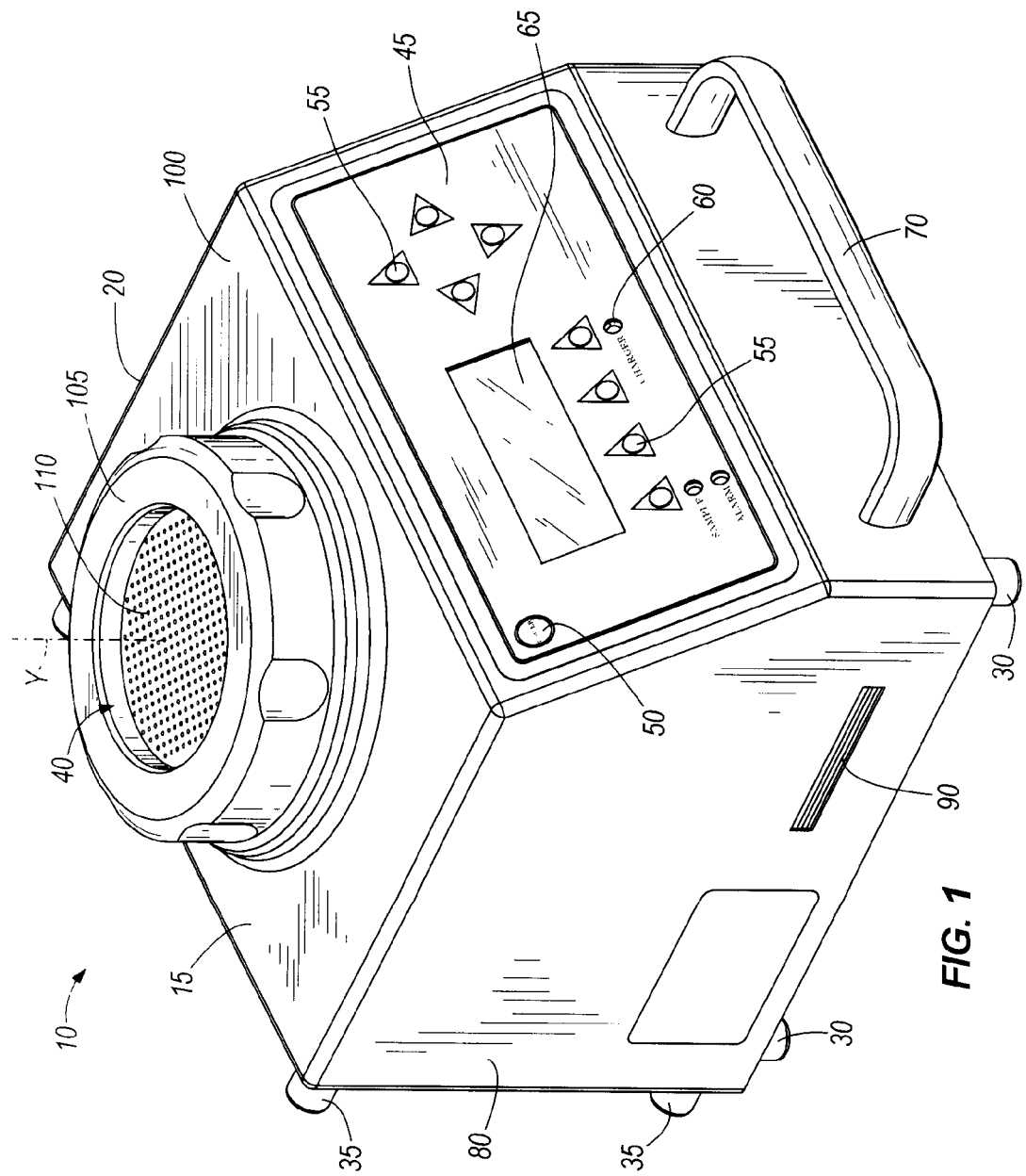
FIG. 1 is a perspective view of a portable gaseous-fluid sampler embodying the present invention.

FIG. 1 illustrates a portable gaseous-fluid sampler 10 operable to collect microbial particles from a gaseous fluid. It is to be understood that microbial particles can include biologically active particles such as bacteria, fungi, and similar particles. Moreover, the term gaseous fluid makes reference to ambient air and other gaseous fluid that may not be considered as ambient air, such as, but not limited to, air in a clean room environment. The portable sampler 10 shown in FIGS. 1-6 is only an exemplary construction, and it is to be understood that other physical appearances fall within the scope of the invention.

Figure 2:
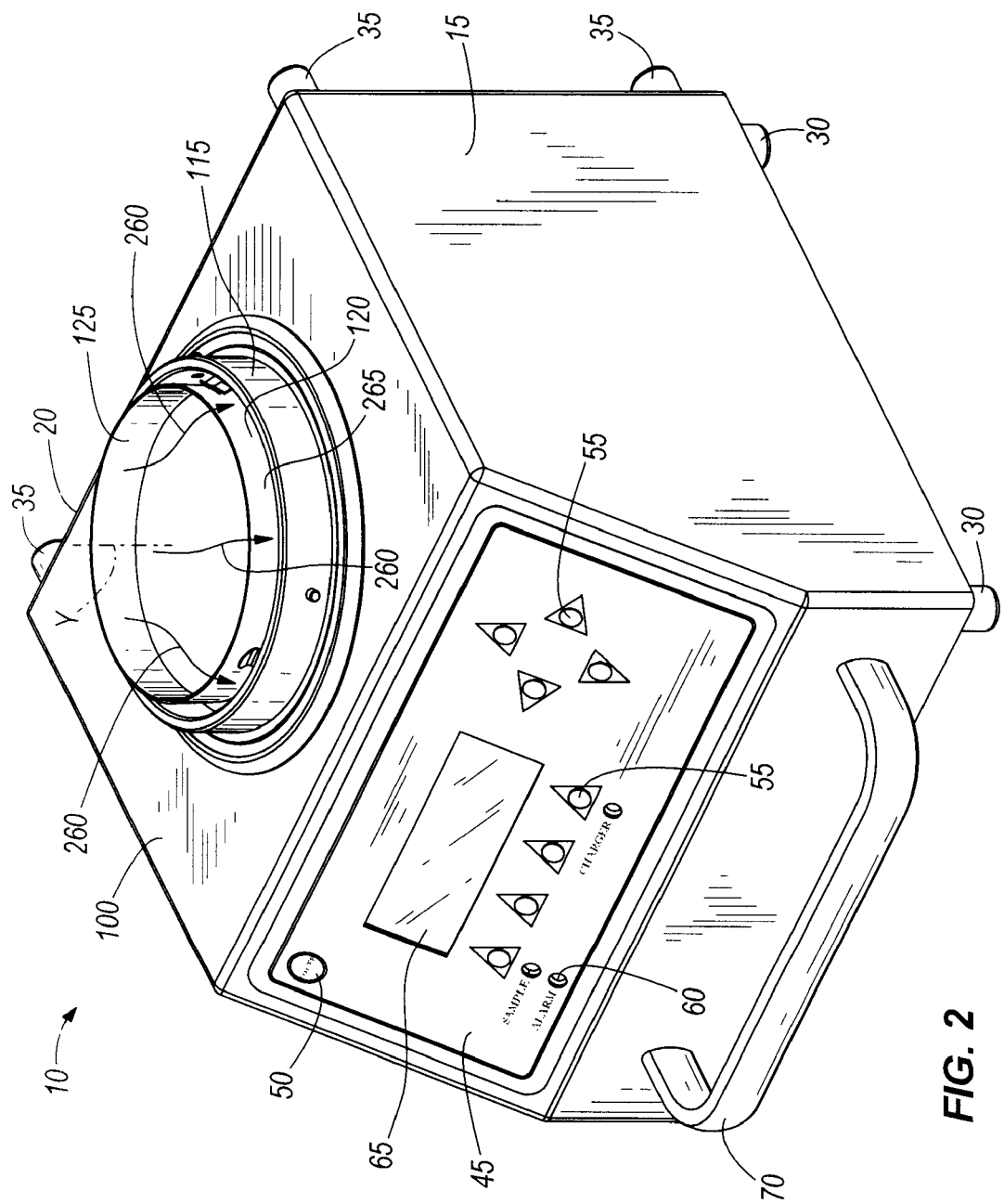
FIG. 2 is another perspective view of the portable gaseous-fluid sampler of FIG. 1 with a cover removed.
Figure 6:
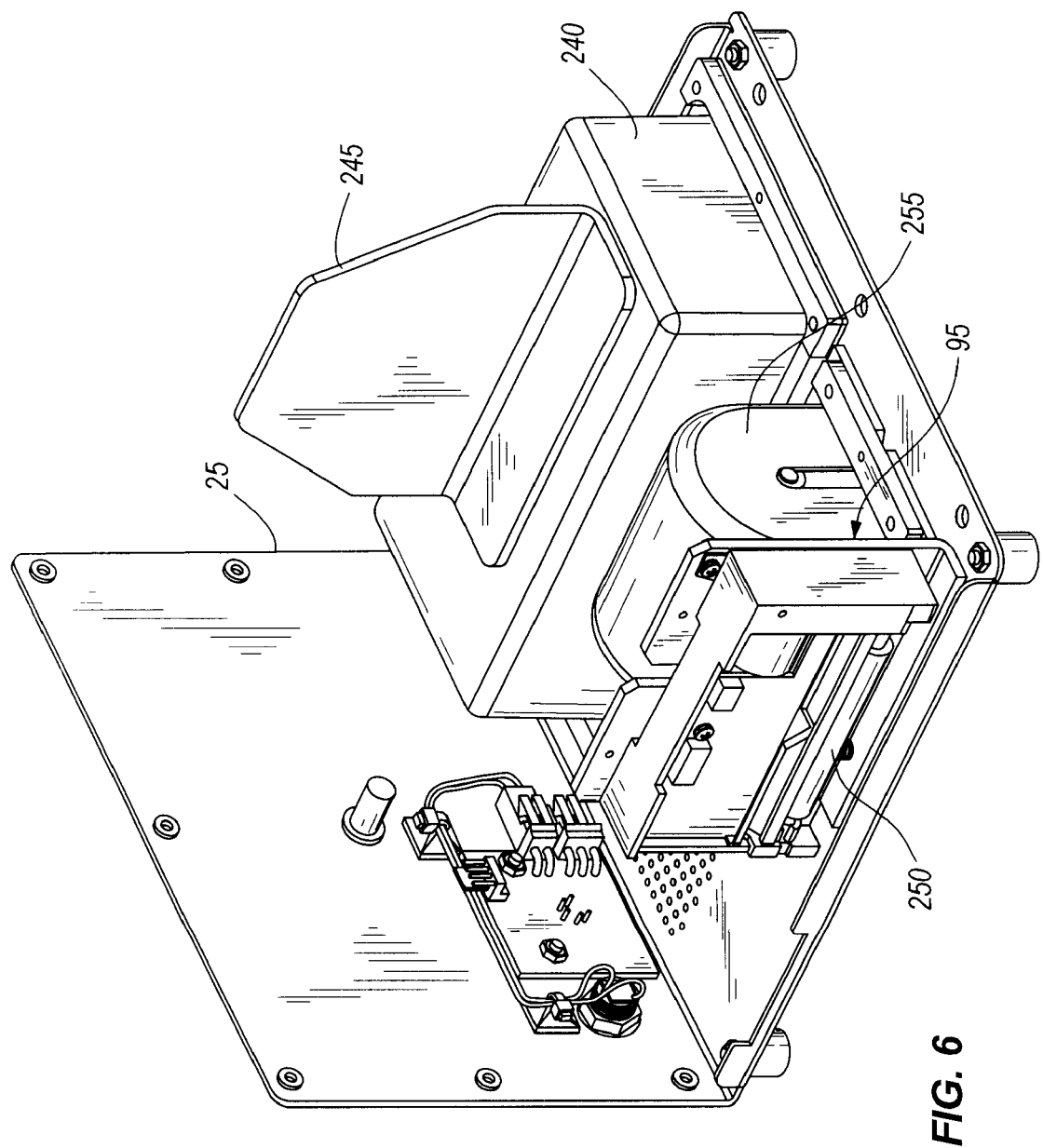
FIG. 6 is a perspective view of the portable gaseous-fluid sampler of FIG. 1 with a top cover removed.

With reference to FIGS. 1-2, the portable sampler 10 includes a support structure, such as a housing 15, which may be divided into a top cover 20 (best shown in FIG. 4) and a bottom cover 25 (best shown in FIG. 6). However, the structure does not need to be the housing 15. Rather, the structure can be an open structure for supporting the gaseous-fluid flow system (discussed below). The portable sampler 10 also includes a first set of supports 30 and a second set of supports 35. The first set of supports 30 helps the portable sampler 10 sit in a first orientation, which is shown in FIGS. 1-2, defining a gaseous fluid intake portion 40 facing upward. The second set of supports 35 helps the portable sampler 10 sit in a second orientation (not shown) defining the intake portion 40 facing sideways. The just-described orientations are relative to the position of the portable sampler 10 within the figures. It is to be understood that the portable sampler 10 may operate at any orientation or angle of the intake portion 40 and need not to be supported by the first set of supports 30 or the second set of supports 35. For example, the portable sampler 10 can include a tripod mount (not shown) to set the portable sampler 10 at an elevated position.

The portable sampler 10 also includes an interface panel 45 for a user to operate the portable sampler 10 and to view information related to the portable sampler 10 and the samples collected by the portable sampler 10. The interface panel 45 includes a power button 50 generally configured to operate the portable sampler 10 between an "on" state and an "off" state. Depending on the configuration of the portable sampler 10, the power button 50 may operate the portable sampler 10 between other states, such as an "idle" state and a "power save" state. The interface panel 45 also includes buttons 55 operable to control other operating characteristics of the portable sampler 10, and LED lights 60 indicating, among other things, when the portable sampler 10 is in an "alarm" mode or when a sample has been collected. The LED lights 60 may be operable to indicate other modes or states of the portable sampler 10. The interface panel 45 also includes an LCD display 65 operable to display information related to the portable sampler 10 and the sample collected by the portable sampler 10. Other constructions of the portable sampler 10 can include different types of displays other than the LCD display 65. Moreover, other constructions of the portable sampler 10 can include different configurations for the interface panel 45.

In the construction shown in FIG. 1, the portable sampler 10 includes a handle 70 mounted to the housing 15. The handle allows a user to transport the portable sampler 10 between different locations. Also shown in FIG. 1, the first side panel 80 includes a printer slot 90, which discharges printed product (e.g., a label) from a printer unit 95 (shown in FIG. 6). The printer slot 90 may be located at a different location of the housing 15 based of the configuration of the portable sampler 10.

The intake portion 40 shown in FIGS. 1-2 is centrally located on a top panel 100 of the housing 15. The construction of the intake portion 40 shown in FIGS. 1-2 is exemplary only and other constructions are possible. The intake portion 40 in FIG. 1 includes a lid or cover 105 having a centrally located porous surface 110 that allows the flow of a gaseous fluid. The porous surface 110 is shown in FIG. 1 as a perforated surface; however, other porous surfaces are possible. The cover 105 is detachably mounted to a locking rim 115 (FIG. 2), which extends upwardly from an intake port 120. The intake portion 40 also includes a contact device 125 supported within the perimeter of the rim 115 and the intake port 120. For example, the contact device 125 call be a 90 mm Petri dish supporting a culture medium. Other constructions of the portable sampler 10 can include other types of contact devices 125. In the illustrated construction, the elements of the intake portion 40 define a substantially circular shape and are positioned concentric with respect to a vertical axis Y centered on the top panel 100. It should be understood, however, that the intake portion 40 is not limited to the just-described elements and not all elements are required in all constructions.

Figure 3:
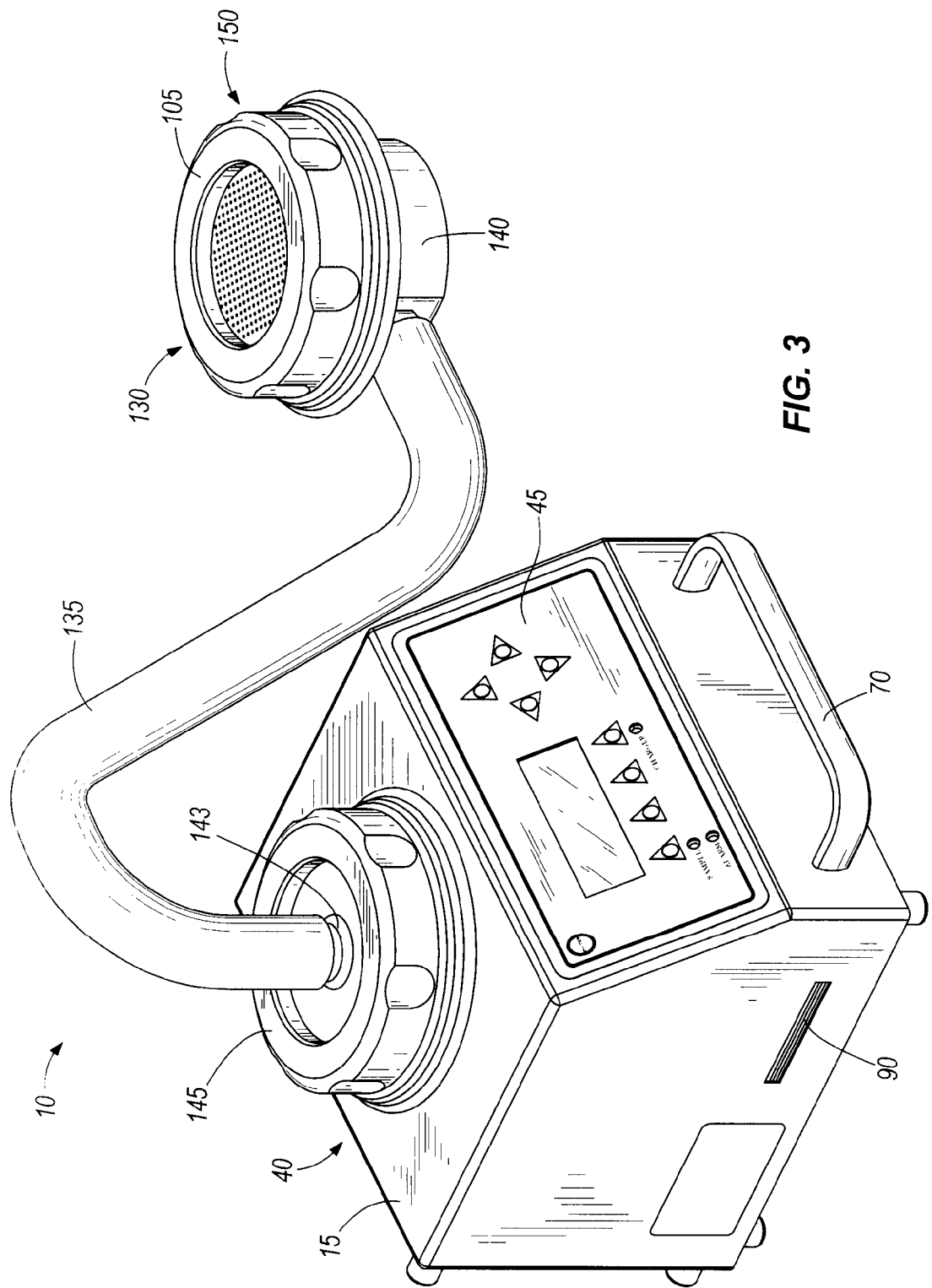
FIG. 3 is the portable gaseous-fluid sampler of FIG. 1 including a remote sampling head.

FIG. 3 illustrates the portable sampler 10 including a base unit, a remote sampling head 130, and a tube 135 fluidly connecting the remote sampling head 130 to the intake portion 40. More specifically, the tube 135 fluidly connects an exhaust or connection portion 140 of the remote sampling head 130 to a port 143 of an adaptor 145 detachably mounted to the intake portion 40. In the construction shown in FIG. 3, the remote sampling head 130 also includes an intake portion 150 having a cover 105 and a contact device (similar to the contact device 125 shown in FIG. 2). A user can transform the portable sampler 10 from the configuration shown in FIGS. 1-2 to the configuration shown in FIG. 3. This transformation includes removing the cover 105 and the contact device 125 from the housing 15, mounting these elements to the remote sampling head 130, and connecting the adaptor 145 to the rim 115. Alternatively, the remote sampling head 130 can include a contact device and a cover with different configurations with respect to the contact device 125 and the cover 105. The tube 135 can be manufactured of a suitable material that allows gaseous-fluid flow. The tube 135 can also be a flexible tube of an appropriate length that allows the remote sampling head to be positioned at a desired, remote location.

Figure 4:
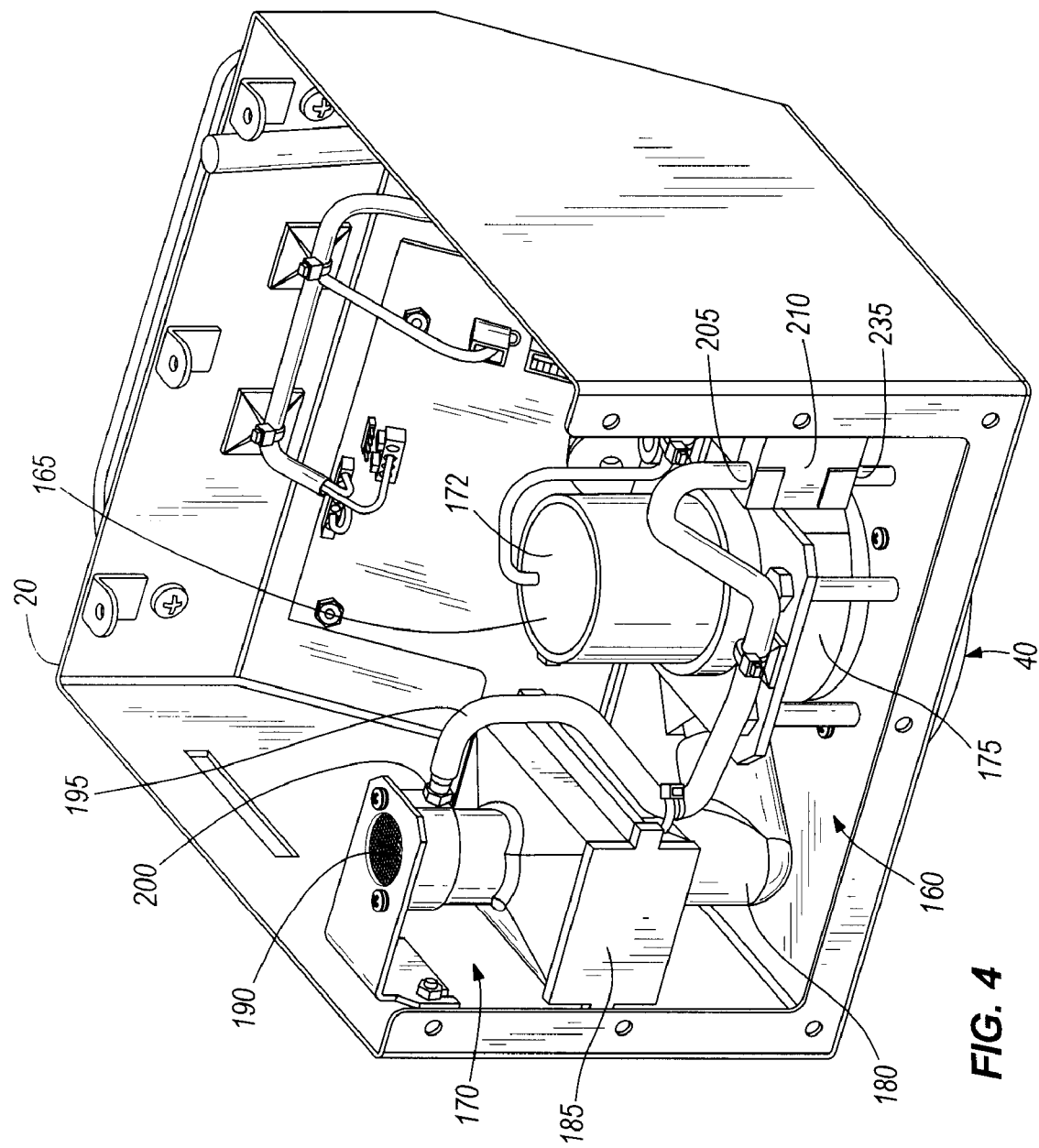
FIG. 4 is a rear, bottom perspective view of the portable gaseous-fluid sampler of FIG. 1 with a bottom cover removed.
Figure 5:
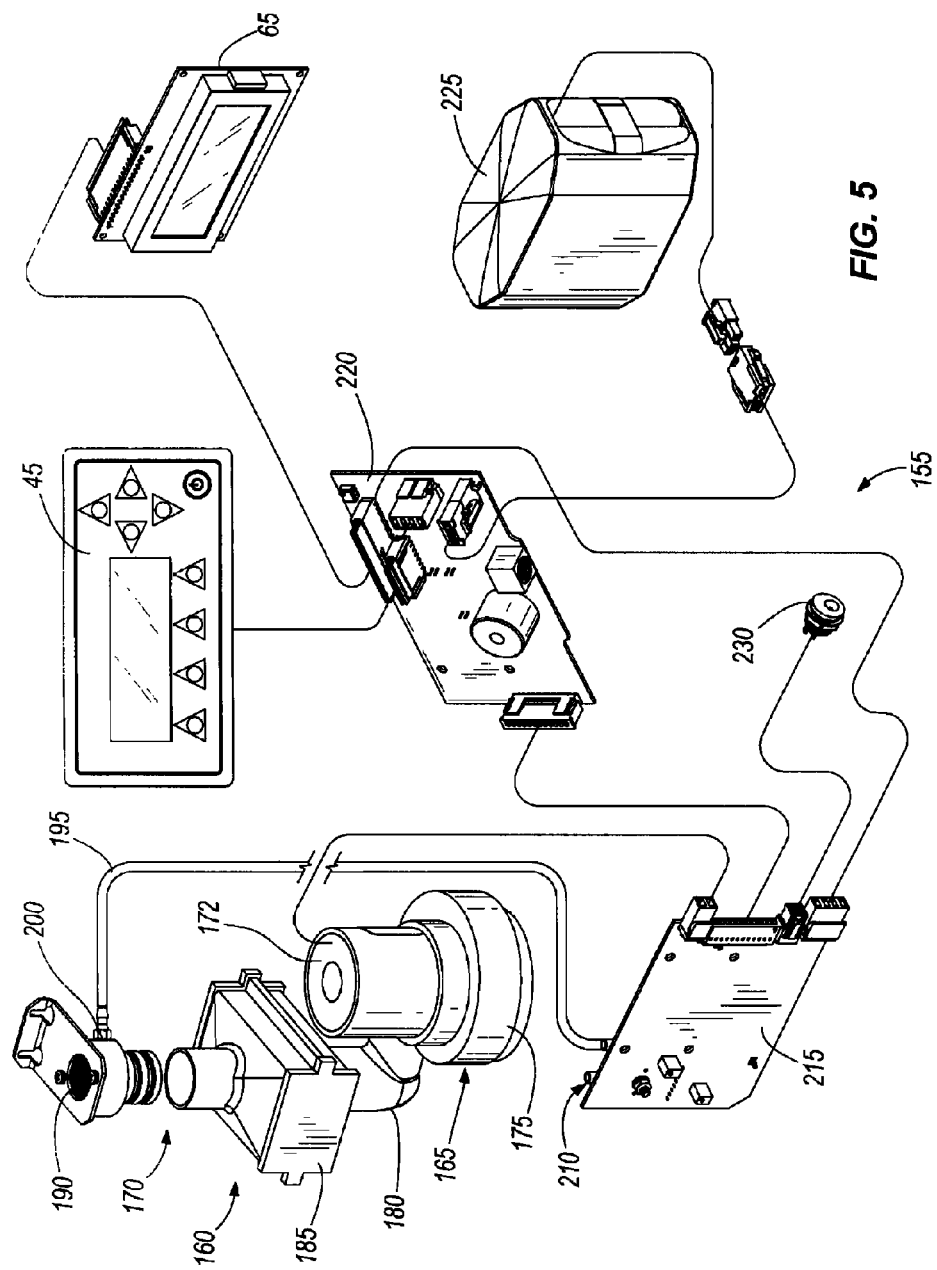
FIG. 5 is a schematic view of various elements of the portable gaseous-fluid sampler of FIG. 1.

With reference to FIGS. 4-5, the portable sampler 10 also includes a control system 155 and a gaseous-fluid flow system 160. The gaseous-fluid flow system 160 includes the intake portion 40, a blower assembly 165, and a gaseous-fluid exhaust portion 170. The blower assembly 165 includes a motor generally within a motor casing 172, and a blower 175 driven by the motor to generate gaseous-fluid flow through the portable sampler 10. The blower assembly 165 is fluidly connected to the intake portion 40, and is also fluidly connected to the exhaust portion 170 with a tube 180. The tube 180 directs gaseous-fluid flow from the blower assembly 165 to an exhaust filter 185 of the exhaust portion 170 and subsequently to an exhaust port 190. The gaseous-fluid flow system 160 also includes a gaseous fluid collecting tube 195 fluidly coupled to a first port 200 substantially adjacent to the exhaust port 190, and to a second port 205 of a sensor. The sensor can be, for example, a mass-flow sensor 210. Alternatively, the sensor can be a differential pressure transducer. The first port 200 is generally downstream in the flow system 160 with respect to the exhaust filter 185. However, other constructions can include the first port 200 located at other locations of the flow system 160. It is also contemplated that additional flow structure can be coupled to the exhaust port 190 for discharging gaseous-fluid flow at a location remote from the exhaust port 190.

With reference to FIG. 5, the control system 155 includes a first circuit board 215, a second circuit board 220, a power source 225, the interface panel 45, and the LCD display 65. The second circuit board 220 is electrically coupled to the first circuit board 215, the control panel 45, the LCD display 65, and the power source 225. The second circuit board 220 includes a controller with a microprocessor and memory to control one or more operations of the portable sampler 10. For example, the second circuit board 220 can be operable to receive instructions through the interface panel 45, display information related to the portable sampler through the LCD display 65, and manage the operation of the portable sampler 10 based on the power supplied by the power source 225. It is to be understood that the second circuit board 220 may be operable to perform other functions and operations not described herein.

The first circuit board 215 is electrically coupled to the second circuit board 220, the blower 165, and a power input jack 230. The first circuit board 215 relays power obtained from the power input jack 230 to the second circuit board 220. The first circuit board also includes the mass-flow sensor 210 (better shown in FIG. 4). The second port 205 and a third port 235 of the mass-flow sensor 210 allows a portion of the gaseous-fluid flow to pass through the mass-flow sensor 210. In some constructions of the portable sampler 10, the mass-flow sensor 210 is a Honeywell AWM92100V sensor. Alternatively, a differential pressure transducer can be coupled to the first circuit board in place of the mass-flow sensor 210. The differential pressure transducer includes the second port 205 for comparing a pressure from the fluid-collecting tube 195 to an ambient pressure at the third port 235.

The first circuit board 215 includes a second controller, such as an analog controller and/or a second microprocessor and memory, either of which operates one or more aspects of the portable sampler 10. The second controller is operable to determine a characteristic of the gaseous fluid and/or the gaseous-fluid flow through the portable sampler 10 (e.g. mass, volume, speed, composition, etc.) based on information generated by the mass-flow sensor 210, the differential pressure transducer, or other input devices not specifically discussed herein. Moreover, the controller of the first circuit board 215 can also be operable to control the portable sampler 10 based on determining the desired characteristic. For example, the controller can be operable to control the motor of the blower assembly 165 to adjust the gaseous-fluid flow through the flow system 160 based on the amount of mass of gaseous fluid flowing through the flow system 160 over a predetermined period of time. Alternatively, the motor can also include a motor controller electrically coupled to the second controller to operate the motor. Similar to the second circuit board 220, the first circuit board 215 may be operable to perform other functions and operations not specifically described herein. Additionally, it should be understood that other suitable configurations of the first circuit board 215 and the second circuit board 220, including the combining of the first and second circuit boards, are possible.

FIG. 6 illustrates the bottom cover 25 including the first circuit board 215 electrically coupled to the power input jack 230, the printer unit 95, and the battery 225 supported within a battery casing 240. A fin 245 can be coupled to the battery casing 240, or any other portion of the housing 15, to help define a space within the housing 15. In this particular construction, the printer unit 95 includes a label printer 250 and a paper supply 255. In other constructions, the printer unit 95 can include other types of printers, other types of paper supply, and other suitable material to allow a user to print information relating to the portable sampler 10 and the characteristics of the gaseous-fluid flow passing through the portable sampler 10. Additionally, the printer unit 95 can be operated by either, or both, the first circuit board 215 and the second circuit board 220.

With reference to FIGS. 1-2, one aspect of the operation of the portable sampler 10 is controlling gaseous-fluid flow through the intake portion 40. Generally, gaseous-fluid flow is generated by operating the blower assembly 165, which causes gaseous fluid to be sucked into the portable sampler 10 through the apertures defined by the cover 105. The configuration of the cover 105 causes gaseous fluid to engage the contact device 125 in a direction substantially parallel to the axis Y. The contact device 125, generally supporting some type of nutrient agar, is allowed to receive or capture biologically active particles present in the gaseous fluid. Subsequently, gaseous-fluid flow continues towards the intake port 120 as indicated by the curved arrows 260. More specifically, gaseous-fluid flow continues from the surface of the contact device 125 to the blower assembly 165 through a ring-shaped aperture 265 defined between the periphery of the contact device 125 and the rim 115.

With reference to FIG. 3, it is envisioned that gaseous-fluid flow would behave in a similar manner as described with respect to the gaseous-fluid flow in FIGS. 1-2. More specifically, gaseous-fluid flow generated by the blower assembly 165 would enter the remote sampling head 130 through the cover 105 and engage the contact device 125 within the remote sampling head 125. The remote sampling head 130 and the tube 135 allow the portable sampler 10 to collect microbial particles at remote locations from the main unit. For example, the remote sampling head 130 can be used at a remote location where the portable sampler 10 does not fit or where an environment is not suitable for a person or for some element of the main unit.

In reference to FIG. 4, the totality of gaseous fluid moves from the blower assembly 165 to the exhaust filter 185 through the tube 180. The exhaust filter 185 filters the gaseous fluid of substantially all microbial particles present in the gaseous fluid prior to releasing a relatively large amount of the gaseous fluid though the exhaust port 190. Generally, about 98% or more of the gaseous-fluid flow is released through the exhaust port 190 and about 2% or less of the gaseous-fluid flow is directed towards the mass-flow sensor 210 from the first port 200 to the second port 205 through the gaseous-fluid collecting tube 195. The mass-flow sensor 210 is operable to determine a characteristic of the gaseous fluid passing through the portable sampler 10 based on the portion of gaseous-fluid flow collected at the first port 200, passing through the second port 205, and being released at the third port 235. The mass-flow sensor 210 can also be operable to generate a signal indicative of a characteristic of the gaseous fluid flowing through the portable sampler 10.

In one example, the mass-flow sensor 210 generates a signal indicative of the mass of gaseous fluid flowing through the portable sampler 10 over a predetermined period of time. The signal generated by the mass-flow sensor 210 can be supplied to a controller to control the operation of the blower assembly 165 and adjust the gaseous-fluid flow to a desired amount. In this particular example, it may be desired to maintain the gaseous-fluid flow at 100 liters per minute (100 LPM). The mass-flow sensor 210 is operable to detect a variation of the gaseous-fluid flow to control the operation of the blower assembly 165 and adjust the gaseous-fluid flow to 100 LPM. It is to be understood that this flow rate is only one example. Moreover, it is possible to operate the blower assembly 165 to generate a variable flow rate over time through the portable sampler. Other desired operations of the blower assembly 165 based on the gaseous-fluid flow rate detected by the mass-flow sensor 210 are possible.

Various features and advantages of the invention are set forth in the following claims.

What is claimed is:

1. A portable microbial gaseous-fluid sampler for collecting microbial particles from gaseous fluid, the sampler comprising:
   a structure;
   a gaseous-fluid flow system at least partially supported by the structure, the gaseous-fluid flow system including a blower having a motor operable to drive the blower and a gaseous-fluid exhaust portion positioned downstream of the blower, the gaseous-fluid exhaust portion having an exhaust port and an exhaust filter operable to substantially filter a totality of a gaseous fluid flowing through the sampler prior to exhausting the gaseous fluid; and
   a control system including a mass-flow sensor to sense a characteristic relating to a gaseous-fluid flow and operable to at least in part control the blower to selectively adjust the gaseous-fluid flow through the sampler based on a signal indicative of the gaseous-fluid flow generated by the mass-flow sensor,
   wherein the gaseous-fluid flow system further includes a sensor portion having a gaseous-fluid collecting tube extending from the exhaust portion, the gaseous-fluid collecting tube directing a portion of the gaseous-fluid flow to the mass-flow sensor of the control system, and wherein the gaseous-fluid collecting tube is coupled to the exhaust portion in a downstream position of the gaseous-fluid flow system with respect to the exhaust filter.

2. The sampler of claim 1, wherein the exhaust filter is coupled substantially adjacent to the exhaust port.

3. The sampler of claim 1, wherein the control system includes a gaseous-fluid flow controller coupled to the mass-flow sensor.

4. The sampler of claim 1, wherein the control system includes a gaseous-fluid flow controller and a differential pressure transducer coupled to the gaseous-fluid flow controller.

5. The sampler of claim 1, wherein the gaseous-fluid flow system further includes a gaseous-fluid intake portion having an intake port in fluid communication with the exhaust port, and wherein the sampler further comprises a remote sampling head at a remote location from the sampler and in fluid communication with the intake port.

6. The sampler of claim 5, wherein the remote sampling head further includes a connecting portion with an exhaust port, and wherein the sampler further comprises an adaptor cover coupled to the gaseous-fluid intake portion, the adaptor cover having a connecting portion including an intake port, and a tube configured to fluidly couple the exhaust port of the remote sampling head with the intake port of the adaptor cover.

7. The sampler of claim 5, wherein the remote sampling head further includes an intake portion configured to receive a contact device to collect the microbial particles.

8. The sampler of claim 5, wherein the exhaust filter is substantially adjacent to the exhaust port.

9. The sampler of claim 5, wherein the exhaust filter is operable to substantially filter a totality of a gaseous fluid through the sampler prior to the gaseous fluid exhausting from the gaseous fluid exhaust portion.

10. The sampler of claim 5, wherein the control system includes a gaseous-fluid flow controller coupled to the mass-flow sensor.

11. The sampler of claim 1, wherein the gaseous-fluid flow system further includes a gaseous-fluid intake portion having an intake port, and wherein the blower is placed adjacent to, and in fluid communication with, the intake port.

12. The sampler of claim 1, wherein the mass-flow sensor generates a signal indicative of the gaseous-fluid flow through the gaseous-fluid collecting tube, and the control system compares the signal with a reference signal.

13. The sampler of claim 11, wherein the control system further includes a gaseous-fluid flow controller coupled to the mass-flow sensor.

14. The sampler of claim 13, wherein the gaseous-fluid flow controller includes an analog gaseous-fluid flow controller.

15. The sampler of claim 11, wherein the control system compares the signal with a reference signal.

16. The sampler of claim 11, wherein the exhaust filter is substantially adjacent to the exhaust port.

17. The sampler of claim 11, further comprising a remote sampling head at a remote location from the portable sampler and in fluid communication with the intake port, the remote sampling head configurable to collect at least a portion of the microbial particles from a sample of the gaseous fluid at the remote location.

18. A portable microbial gaseous-fluid sampler for collecting at least a portion of the microbial particles present in a gaseous fluid, the sampler comprising:

a structure;

a gaseous-fluid flow system at least partially supported by the structure, the gaseous-fluid flow system including a blower having a motor operable to drive the blower and a gaseous-fluid exhaust portion positioned downstream of the blower, the gaseous-fluid exhaust portion having an exhaust port and a microbial exhaust filter operable to substantially filter a totality of the microbial particles present in the gaseous fluid flowing through the sampler prior to exhausting the gaseous fluid; and a control system including a mass-flow sensor to sense a characteristic relating to a gaseous-fluid flow and operable to at least in part control the blower to selectively adjust the gaseous-fluid flow through the sampler based on a signal indicative of the gaseous-fluid flow generated by the mass-flow sensor, wherein the gaseous-fluid flow system further includes a sensor portion having a gaseous-fluid collecting tube extending from the exhaust portion, the gaseous-fluid collecting tube directing a portion of the gaseous-fluid flow to the mass-flow sensor of the control system, and wherein the gaseous-fluid collecting tube is coupled to the exhaust portion in a downstream position of the gaseous-fluid flow system with respect to the microbial exhaust filter.

* * * * *

UNITED STATES PATENT AND TRADEMARK OFFICE
CERTIFICATE OF CORRECTION

| | | |
|---|---|---|
| PATENT NO. | : 7,752,930 B2 | Page 1 of 1 |
| APPLICATION NO. | : 11/549259 | |
| DATED | : July 13, 2010 | |
| INVENTOR(S) | : Kreikebaum et al. | |

It is certified that error appears in the above-identified patent and that said Letters Patent is hereby corrected as shown below:

Col. 7 line 46
Claim 12, line 1:

"The sampler of claim 1, wherein the mass-flow sensor" should be --The sampler of claim 11, wherein the mass-flow sensor--

Signed and Sealed this
Twenty-eighth Day of June, 2011

David J. Kappos
*Director of the United States Patent and Trademark Office*